(12) United States Patent
Schehlmann et al.

(10) Patent No.: US 6,482,394 B1
(45) Date of Patent: Nov. 19, 2002

(54) PROPELLANTLESS PUMP SPRAYS AND PUMP FOAMS CONTAINING AN ANIONIC COPOLYMER OF METHACRYLIC ACID AND ETHYL ACRYLATE

(75) Inventors: Volker Schehlmann, Römerberg; Peter Hössel, Schifferstadt, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/530,372

(22) PCT Filed: Nov. 4, 1998

(86) PCT No.: PCT/EP98/07027

§ 371 (c)(1),
(2), (4) Date: Apr. 27, 2000

(87) PCT Pub. No.: WO99/25311

PCT Pub. Date: May 27, 1999

(30) Foreign Application Priority Data

Nov. 14, 1997 (DE) .......................... 197 50 520

(51) Int. Cl.$^7$ ............................ A61K 7/00; A61K 9/00
(52) U.S. Cl. .................. 424/47; 424/70.11; 424/70.15; 424/70.16; 424/70.22; 424/70.29; 514/945
(58) Field of Search ............................ 424/47, DIG. 1, 424/DIG. 2, 70.11, 70.15, 70.16, 70.22, 70.27; 514/945, 944

(56) References Cited

U.S. PATENT DOCUMENTS

| | | | |
|---|---|---|---|
| 4,009,256 A | * | 2/1977 | Nowak et al. |
| 4,638,822 A | * | 1/1987 | Grollier et al. |
| 5,879,669 A | | 3/1999 | Clausen et al. |

FOREIGN PATENT DOCUMENTS

| | | |
|---|---|---|
| BR | 9305781-4 | 2/1997 |
| DE | 42 39 499 | 5/1994 |
| DE | 4315405 | 11/1994 |
| FR | 2 760 360 | 9/1998 |
| GB | 2134784 | 8/1984 |
| WO | 94/02115 | 2/1994 |
| WO | 94/12147 | 6/1994 |
| WO | 94/26235 | 11/1994 |
| WO | 98/38969 | 9/1998 |

* cited by examiner

Primary Examiner—Dameron L. Jones
(74) Attorney, Agent, or Firm—Keil & Weinkauf

(57) ABSTRACT

Hair treatment compositions in the form of pump sprays and pump foams that are free from propellant gases comprise at least one cationic and at least one anionic polymer having methacrylic and ethyl units.

4 Claims, No Drawings

PROPELLANTLESS PUMP SPRAYS AND PUMP FOAMS CONTAINING AN ANIONIC COPOLYMER OF METHACRYLIC ACID AND ETHYL ACRYLATE

FIELD OF THE INVENTION AND DESCRIPTION OF RELATED ART

The present invention relates to pump sprays, pump foams and leave-on hair treatment compositions all of which are free from propellant gas and comprise anionic and cationic polymers. U.S. Pat. No. 4,240,450 discloses mixtures and processes for treating keratin materials with polymers. The mixtures comprise an anionic and a cationic polymer. In many of the known mixtures this results in problems, in that the polymers are precipitated as solids in the mixtures. This necessitates a special application method. The known mixtures are intended in particular for what are known as rinse-off products, i.e. compositions, such as shampoos, which are applied and then washed off again. As compositions which remain on the hair only lotions are mentioned in column 51. Compositions which are free from propellant gas and are sprayed onto the hair are not disclosed. A host of very widely differing compounds are mentioned as possible polymers.

DE 32 17 059 C2 describes pressurized compositions for applying to hair that are in the form of an aerosol foam, with aerosol foam denoting a foam obtained with the aid of a conditioned agent which is under pressure. These compositions necessarily include a propellant. The use of propellants, however, is to be avoided on environmental grounds.

It is an object of the present invention to provide hair treatment compositions which can be applied by spraying even without a propellant gas, which are readily distributed on the hair, and which even under conditions of high atmospheric humidity provide a high level of stability to the hairstyle and at the same time permit good dry combability and elasticity of the hair. The intention is at the same time to ensure that a stable foam can be produced and that the compositions as leave-on products, i.e. as compositions which remain on the hair and are not washed off again after use, impart high flexural strength and little stickiness to the hair.

BRIEF SUMMARY OF THE INVENTION

We have found that this object is achieved in accordance with the invention by hair treatment compositions in the form of pump sprays and pump foams that are free from propellant gas and comprise at least one cationic and at least one anionic polymer.

The hair treatment compositions of the invention in the form of pump sprays and pump foams surprisingly allow access, even without the use of the unwanted propellants, to sprayable compositions which lead to stable and yet light and readily distributed foams that feature good wet and dry combability and hairsetting and which improve the flexural strength of the hair without the occurrence of stickiness.

The hair treatment compositions of the invention can also be in the form of leave-on hair treatment compositions which are free from propellant gas and from polysiloxane and which comprise, dissolved in a solvent, a copolymer with vinylpyrrolidone units and a copolymer with methacrylic acid and ethyl acrylate units.

DETAILED DESCRIPTION OF THE INVENTION

As the polymers it is possible to employ a large number of compounds which are known per se, for example, from DE 32 17 059.

Preference is given to the use of cationic polymers having a molecular weight ($M_n$) of from 500–1,000,000 and comprising primary, secondary, tertiary and/or quaternary amine groups. As anionic polymers it is preferred to employ polymers having a molecular weight ($M_n$) of from 500 to 1,000,000 which comprise sulfo, carboxyl or phosphoric acid groups.

Use is made in particular of cationic polymers of the following groups, which are mentioned in DE 32 17 059:

1) copolymers of vinylpyrrolidone-dialkylaminoalkyl methacrylate or acrylate which are unmodified or quaternized, 2) derivatives of cellulose ethers comprising quaternary ammonium groups, and quaternary cellulose derivatives, 3) cationic polysaccharides and cationic guar gum derivatives, 4) 
   cationic polymers selected from the group of polymers comprising groups of the formula —A—Z—A—Z— (I) in which A is a radical having two amino groups, preferably piperazinyl, and Z is B or B' which are identical or different and are a linear or branched alkylene which is unsubstituted or substituted by hydroxyls and which may also include oxygens, nitrogens, sulfurs and/or from one to three aromatic and/or heterocyclic rings;
   polymers of the formula —A—$Z_1$—A—$Z_1$— (II) in which A is as defined above and $Z_1$ is $B_1$ or $B'_1$ and on at least one occasion is $B'_1$, where $B_1$ is a linear or branched alkylene or hydroxyalkylene, $B'_1$ is a linear or branched alkylene which is unsubstituted or substituted by one or more hydroxyls and is interrupted by one or more nitrogens, the nitrogen being substituted by an alkyl chain which is uninterrupted or interrupted by an oxygen and which if desired includes one or more hydroxyls;
   alkylation products with alkyl or benzyl halides, loweralkyl-tosylate or -mesylate, and oxidation products of the polymers of the formulae (I) and (II), 5) polyamino-polyamides, 6) crosslinked polyamino-polyamides from the following group
   a) crosslinked, alkylated or nonalkylated polyaminopolyamides obtained by crosslinking a polyaminopolyamide prepared by polycondensation of an acidic compound and a polyamine with a crosslinking agent from the group of the epihalohydrins, diepoxides, dianhydrides, unsaturated anhydrides and bis-unsaturated derivatives, the crosslinking agent being used in amounts of from 0.025 to 0.35 mol per amine group of the polyaminoamide;
   b) crosslinked polyamino-polyamides obtained by crosslinking a polyamino-polyamide as defined above with a crosslinking agent selected from the following group:
      I bis-halohydrins, bis-azetidinium, bis-haloacyldiaminee, alkyl bis-halides,
      II oligomers obtained by reacting a compound of group or epihalohydrins, diepoxides and/or bis-unsaturated derivatives with a bifunctional compound that is reactive toward these compounds,
      III quaternization products of a compound of group I and of the oligomers of group II which comprise tertiary amine groups some or all of which are alkylatable with an alkylating agent, crosslinking being effected with the aid of from 0.025 to 0.35 mol-% of crosslinking agent per amine group of the polyaminoamide, c) polyamino-polyamide derivatives obtained by condensing a polyalkylene-polyamine with a polycarboxylic acid and then alkylating the product using bifunctional agents of the type of the adipic acid-dialkylaminohydroxyalkyl-dialkylenetriamine copolymers, 7) polymers obtainable by (i) free-radically initiated copolymerization of monomer mixtures comprising
(a) from 1 to 99.99% by weight, preferably from 2 to 70% by weight and, with particular preference, from 2 to 50% by weight of a cationic monomer or quaternizable monomer,
(b) from 0 to 98.99% by weight, preferably from 22 to 97.98% by weight and, with particular preference, from 45 to 97.95% by weight of a water-soluble monomer,
(c) from 0 to 50% by weight, preferably from 0 to 40% by weight, with particular preference, from 0 to 30% by weight of a further free-radically copolymerizable monomer, and
(d) from 0.01 to 10% by weight, preferably from 0.02 to 8% by weight, and, with particular preference, from 0.05 to 5% by weight of a bifunctional or higher polyfunctional, free-radically copolymerizable monomer, and (ii) subsequent quaternization of the polymer if the monomer (a) employed was a non-quaternized monomer.

Suitable monomers (a) are the N-vinylimidazole derivatives of the formula (I) where $R^1$ to $R^3$ are hydrogen, $C_1$–$C_4$-alkyl or phenyl

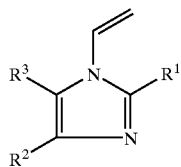

(I)

Also suitable are diallylamines of the formula (II) where $R^4$ is $C_1$–$C_{24}$-alkyl.

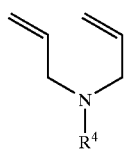

(II)

Also suitable are N,N-dialkylaminoalkyl acrylates and methacrylate, and N,N-dialkylaminoalkylacrylamides and methacrylamides, of the formula (III),

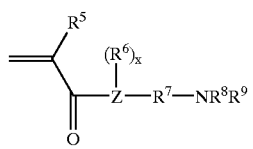

(III)

where $R^5$ and $R^6$ independently are hydrogen or methyl, $R^7$ is $C_1$–$C_{24}$-alkylene optionally substituted by alkyls and $R^8$ and $R^9$ are $C_1$–$C_{24}$-alkyl, Z being a nitrogen together with x=1 or an oxygen together with x=0.

The quaternization of the monomer or of a polymer with one of these quaternizing agents can take place in accordance with conventional methods.

Preferred quaternizing agents are methyl chloride, dimethyl sulfate or diethyl sulfate.

Preferred examples of monomers (a) are 3-methyl-1-vinylimidazolium chloride and methosulfate, dimethyldiallylammonium chloride and also N,N-dimethylaminoethyl methacrylate and N-[3-(dimethylamino)propyl] methacrylamide which have been quaternized by methyl chloride, dimethyl sulfate or diethyl sulfate.

Suitable water-soluble monomers (b) are N-vinyllactams, eg. N-vinylpiperidone, N-vinylpyrrolidone and N-vinylcaprolactam, N-vinylacetamide, N-methyl-N-vinylacetamide, acrylamide, methacrylamide, N,N-dimethylacrylamide, N-methylolmethacrylamide, N-vinyloxazolidone, N-vinyltriazole, hydroxyalkyl (meth)acrylates, eg. hydroxyethyl (meth)acrylate and hydroxypropyl (meth)acrylates, or alkyl ethylene glycol (meth)acrylates having 1 to 50 ethylene glycol units in the molecule.

Suitable monomers (c) are $C_1$–$C_{24}$-, especially $C_1$–$C_{10}$-alkyl esters of (meth)acrylic acid, e.g. methyl (meth)acrylate, ethyl (meth)acrylate, tert-butyl (meth)acrylate, isobutyl (meth)acrylate, n-butyl (meth)acrylate and acrylamides such as N-tert-butylacrylamide or N-tert-octylacrylamide. Also suitable are vinyl esters of carboxylic acids, eg. vinyl acetate or vinyl propionate.

Monomers (d), which possess a crosslinking function, are compounds having at least 2 ethylenically unsaturated, nonconjugated double bonds in the molecule.

Suitable crosslinkers are, for example, acrylic esters, methacrylic esters, allyl ethers or vinyl ethers of at least dihydric alcohols. The OH groups of the parent alcohols may be in fully or partially etherified or esterified form; however, the crosslinkers contain at least two ethylenically unsaturated groups.

Further suitable crosslinkers are the vinyl esters or the esters of monohydric unsaturated alcohols with ethylenically unsaturated $C_3$–$C_6$ carboxylic acids, for example acrylic, methacrylic, itaconic, maleic or fumaric acid.

Other suitable crosslinkers are esters of unsaturated carboxylic acids with the polyhydric alcohols described above, examples being those of oleic acid, crotonic acid, cinnamic acid or 10-undecenoic acid.

The monomers (a) to (d) can in each case be employed individually or in a mixture with other monomers from the same group.

8) Polymers obtained by reacting a polyalkylenepolyamine which comprises two primary amine groups and at least one secondary amine group with a dicarboxylic acid from the group of diglycolic acid and saturated aliphatic dicarboxylic acids having 3 to 8 carbons, the molar ratio of polyalkylenepolyamine to dicarboxylic acid being from 0.8:1 to 1.4:1; the polyamide formed is reacted with epichlorohydrin in a molar ratio of epichlorohydrin to secondary amine group of the polyamide of from 0.5:1 to 1.8:1, 9) copolymers comprising as main chain constituent units of the formula (III) or (III')

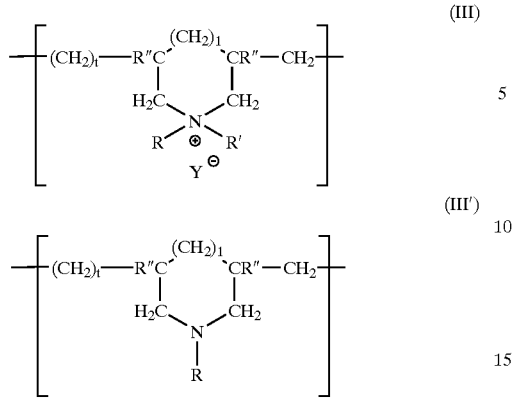

(III)

(III')

where 1 and t are 0 or 1 and 1+t=1, R" is hydrogen or methyl, R and R' independently of one another are alkyl of 1 to 22 carbons, hydroxyalkyl preferably of 1 to 5 carbons, or a lower amidoalkyl group and where R and R' together with the nitrogen to which they are attached can be heterocyclic groups, such as piperidyl or morpholinyl, and also the copolymers comprising units of the formula (III) or (III') and units derived preferably from acrylamide or diacetoneacrylamide, and $Y^\ominus$ is an anion, such as bromide, chloride, acetate, borate, citrate, tartrate, bisulfate, bisulfite, sulfate or phosphate, 10) quaternary polyammonium compounds of the formula

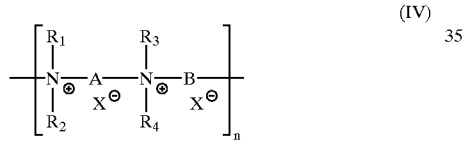

(IV)

where $R_1$ and $R_2$, $R_3$ and $R_4$, which are identical or different, are aliphatic, alicyclic or arylaliphatic radicals of not more than 20 carbons or are lower hydroxyaliphatic radicals, or $R_1$ and $R_2$ and $R_3$ and $R_4$, together or separately, with the nitrogen to which they are attached form heterocyclic rings which if desired include a second heteroatom other than nitrogen, or $R_1$, $R_2$, $R_3$ and $R_4$ are the following group

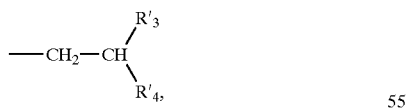

where $R'_3$ is hydrogen or lower alkoxyl, $R'_4$ has the following definitions:

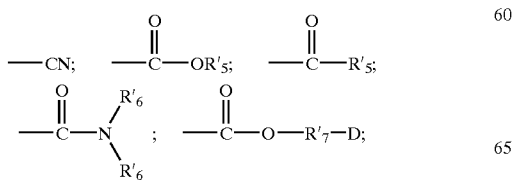

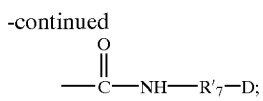

in which $R'_5$ is lower alkyl, $R'_6$ is hydrogen or lower alkyl, $R'_7$ is alkylene and D is a quaternary ammonium group; A and B can be polymethylene groups containing 2 to 20 carbon atoms and being linear or branched, saturated or unsaturated, and incorporated into the main chain there may be one or more aromatic rings such as the following group:

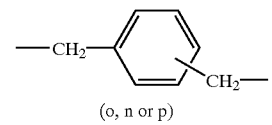

(o, n or p)

one or more groups —CH$_2$—Y—CH$_2$— where Y has the following definitions: O, S, SO, SO$_2$,

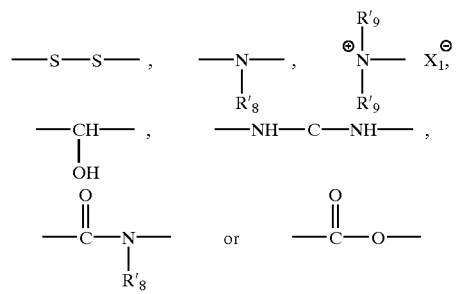

where $X^\ominus_1$ is an amine derived from an organic or inorganic acid, $R'_8$ is hydrogen or lower alkyl, $R'_9$ is lower alkyl, or A and $A_1$ and $R_3$, together with the two atoms to which they are attached, form a piperazine ring; if, moreover, A is linear or branched, saturated or unsaturated alkylene or hydroxyalkylene then B can also denote the following group:
—(CH$_2$)$_n$—CO—D—OC—(CH$_2$)$_n$, where D has the following definition:

a) a glycol radical of the formula —O—I—O— in which Z is a linear or branched hydrocarbon radical or a group corresponding to the following formulae:

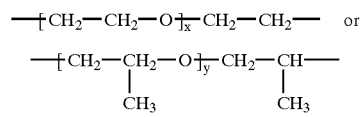

in which x and y are an integer from 1 to 4, which denotes a defined and single degree of polymerization, or are any number from 1 to 4, which denotes an average degree of polymerization;

b) a bis-secondary diamine radical, such as a piperazine derivative, c) a bis-primary diamine radical of the formula:
—NH—Y—NH—, in which Y is a linear or branched hydrocarbon radical or the bivalent radical —CH$_2$—CH$_2$—S—S—CH$_2$—CH$_2$—, d) a urea-derived group of the formula —NH—CO—NH—;

n is chosen so that the molecular mass is generally from 1000 to 100,000,

X$^-$ is an anion, 11) homopolymers or copolymers which are derived from acrylic or methacrylic acid and comprise at least one group of the following formulae:

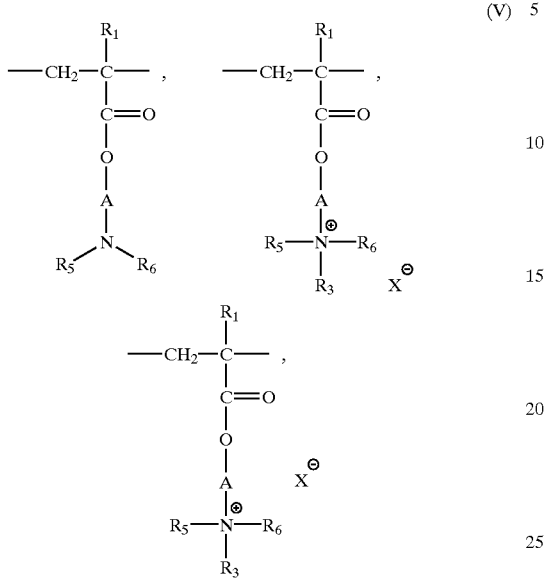

in which $R_1$ is hydrogen or $CH_3$; A is linear or branched alkyl of 1 to 6 carbons or a hydroxyalkyl of 1 to 4 carbons; $R_2$, $R_3$ and $R_4$, which are identical or different, are an alkyl of 1 to 18 carbons or a benzyl; $R_5$ and $R_6$ are hydrogen or alkyl of 1 to 6 carbons; $X^-$ is a methosulfate anion or halide, 12) quaternary copolymers of vinylpyrrolidone-vinylimidazole,
13) polyalkyleneimines,
14) polymeres comprising vinylpyridine or vinylpyridinium groups in the chain,
15) condensates of polyamines and epichlorohydrin,
16) quaternary polyurea compounds (polyureylenes),
17) chitin derivatives,
18) cationic silicone polymers (polymeres silicones).

Polymers selected as the anionic polymer are in particular those from the following group:

polymers comprising carboxyl groups derived from unsaturated mono- or dicarboxylic acids of the following formula:

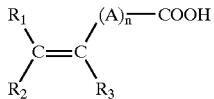

in which n is an integer from 0 to 10, A is a methylene group which may be attached to the carbon of the unsaturated group or to an adjacent methylene group, if n is greater than 1, by way of a heteroatom such as oxygen, sulfur, $R_1$, hydrogen, phenyl or benzyl, $R_2$ is hydrogen, lower alkyl or carboxyl, and $R_3$ is hydrogen, lower alkyl, —$CH_2$—COOH, phenyl or benzyl, polymers which comprise groups derived from sulfonic acids, such as vinylsulfonic, styrenesulfonic, lignosulfonic and naphthalenesulfonic (acid) groups.

Of these, particular preference is given to anionic polymers from the following groups:

A) homo- or copolymers of acrylic or methacrylic acid or salts thereof, copolymers of acrylic acid and acrylamide and salts thereof; sodium salts of polyhydroxycarboxylic acids, B) copolymers of acrylic or methacrylic acid with a monoethylene monomer which may have been grafted with a polyalkylene glycol and which may be branched; copolymers of the type comprising in their chain an unsubstituted or N-alkylated and/or hydroxyalkylated acrylamide group, C) copolymers which are derived from crotonic acid and which include in their chain vinyl acetate or vinyl propionate groups with or without other monomers, such as allyl or methallyl esters, vinyl ethers or vinyl esters of a linear or branched saturated carboxylic acid having a long hydrocarbon chain, it being possible for these polymers, if desired, to have been grafted or crosslinked, D) polymers derived from maleic, fumaric and itaconic acids or their anhydrides with vinyl esters, vinyl ethers, vinyl halides, phenylvinyl derivatives, acrylic acid and esters thereof; copolymers of maleic acid, citraconic anhydride, itaconic anhydride and an allyl or methallyl ester of an α-olefin, acrylic or methacrylic esters, acrylic or methacrylic acid or vinylpyrrolidone in their chain, it being possible for the anhydride groups to be in monoesterified or monoamidated form, E) polyacrylamides comprising carboxylate groups.

The hair treatment compositions of the invention are soluble in water, alcohols or water/alcohol mixtures and are therefore easy to apply to the hair. In particular it has been found that despite the anionic or cationic nature of the individual polymers the solubility of the polymer mixture in alcohols is good and that there are no instances of precipitation at the polymer concentrations customary for these compositions. As a result, the compositions are highly suitable for use as VOC 55 or VOC 80 compositions, in other words as mixtures containing alcohols in defined amounts (55 or 80%), respectively.

Particularly suitable alcohols are monoalcohols such as $C_1$–$C_6$-alkanols, especially ethanol or isopropanol, polyalcohols, such as alkylene glycols, especially ethylene glycol, and also glycol ethers and esters having hydroxyl groups.

The pump sprays and pump foams of the invention generally include neutralizing agents such as 2-amino-2-methyl-1-propanol or triethanolamine, for example, in an amount, for example, of from 0.1 to 1% by weight.

Further auxiliaries can also be added to the compositions of the invention, examples being colorants, preservatives, emulsifiers, fragrances, electrolytes, viscosity regulators, foam stabilizers and further customary cosmetic base materials.

The compositions of the invention may also include further polymers in order, for example, to enhance the film-forming properties.

Preferred anionic polymers employed are copolymers of unsaturated mono- or dicarboxylic acids with $C_1$–$C_4$-alkyl esters or with methacrylic or acrylic acid, especially copolymers comprising methacrylic acid and ethyl acrylate units.

Preferred cationic polymers which are employed are copolymers having vinylpyrrolidone units, especially copolymers with vinylcaprolactam and vinylimidazolium methyl sulfate (Polyquaternium 46).

Overall, the polymers are present in the mixtures of the invention in a concentration of from 0.1 to 12% by weight; the cationic polymers in a concentration of from 0.05 to 5 and the anionic polymers in a concentration of from 0.05 to 7% by weight.

The invention additionally provides leave-on hair treatment compositions which are free from propellant gases and from polysiloxane and which comprise in combination, dissolved in a solvent, a copolymer having vinylpyrrolidone units and a copolymer having methacrylic acid and ethyl acrylate units. The statements made above regarding the solvents, stabilizers, auxiliaries and concentrations apply analogously to these hair treatment compositions.

The leave-on hair treatment compositions, i.e. compositions which remain in the hair after use, are preferably in the form of lotions or gels. For these compositions it is particularly important that they achieve strength while avoiding stickiness.

The pH of the hair treatment compositions of the invention is preferably from 5 to 8, in particular from 5 to 7.

The foams produced with the pump foams of the invention are notable for the fact that although they are stable they do not have too firm a consistency; in other words, when applied to the hair they are soft and can be distributed easily. This property is of particular importance in terms of consumer acceptance.

EXAMPLES

TABLE 1

Examples of pump foam formulations[1]

| Base material Amounts in g | Example 1 | Example 2 | Example 3 | Example 4 | Example 5 | Example 6 | Example 7 |
|---|---|---|---|---|---|---|---|
| Luvimer MAE 30 D (MAA/EA copolymer) | 3.33 (1% a.i.[2]) | 3.33 (1% a.i.) | 3.33 (1% a.i.) | 3.33 (1% a.i.) | 3.33 (1% a.i.) | 3.33 (1% a.i.) | 3.33 (1% a.i.) |
| 2-Amino-2-methyl-1-propanol | 0.26 | 0.35 | 0.26 | 0.35 | 0.35 | 0.26 | 0.26 |
| Luviquat MS 370 (Polyquaternium-44) | 1.25 (0.5% a.i.) | — | — | — | — | — | — |
| Luviquat FC 370 (Polyguaternium-16) | — | 1.25 (0.5% a.i.) | — | — | — | — | — |
| Luviquat Hold (Polyquaternium-46) | — | — | 2.50 (0.5% a.i.) | — | — | — | — |
| Luviquat PQ 11 (Polyquaternium-11) | — | — | — | 2.50 (0.5% a.i.) | — | — | — |
| Ucare Polymer JR 400 (Polyquaternium-10) | — | — | — | — | 0.50 (0.5% a.i.) | — | — |
| Celquat H 100 (Polyquaternium-4) | — | — | — | — | — | 0.50 (0.5% a.i.) | — |
| Jaguar C 14 S (Cationic guar gum) | — | — | — | — | — | — | 0.50 (0.5% a.i.) |
| Cremophor[3] A 25 | 0.50 | 0.50 | 0.50 | 0.50 | 0.50 | 0.50 | 0.50 |
| Tego-Betain[4] L7 | 1.00 | 1.00 | 1.00 | 1.00 | 1.00 | 1.00 | 1.00 |
| Cremophor[5] RH 40 | 0.70 | 0.70 | 0.70 | 0.70 | — | 0.70 | 0.70 |
| Perfume oil Cinderella | 0.20 | 0.20 | 0.20 | 0.20 | 0.20 | 0.20 | 0.20 |
| Preservative K 100 | 0.10 | 0.10 | 0.10 | 0.10 | 0.10 | 0.10 | 0.10 |
| Water | ad 100.00 g | ad 100.00 g | ad 100.00 g | ad 100.00 g | ad 100.00 g | ad 100.00 g | ad 100.00 g |

[1]Pump system: Airspray, model F2 Finger Pump Foamer
[2]a.i.: Content of active ingredient
[3]$C_{16-18}$ fatty alcohol ethoxylate with 25 parts of EO
[4]Cocamidopropyl betaine
[5]Hydrogenated castor oil Chemical Composition of the Polymers
Luvimer 100 P and Luvimer 36 D
   Copolymer of methacrylic acid (MAA)/ethyl acrylate (EA)/t-butyl acrylate (t-BA) 23:10:67
Luvimer MAE 30 D
   Copolymer of MAA/EA approx. 50:50
Luviquat Hold (Polyquaternium-46)
   Copolymer of vinylcaprolactam/vinylpyrrolidone (VP)/3-methyl-1-vinylimidazolium methyl sulfate (QVI) 50:40:10
Luviquat MS 370 (Polyquaternium-44)
   Copolymer of VP/QVI 70:30

Luviquat FC 370 (Polyquaternium-16)
  Copolymer of VP/3-methyl-1-vinylimidazolium chloride 70:30
Luviquat PQ 11 (Polyquaternium-11)
  Copolymer of VP/dimethyl sulfate-quaternized dimethylaminoethyl methacrylate 2:1
Ucare Polymer JR 400 (Polyquaternium-10)
  Cationically modified hydroxyethylcellulose prepared by reaction with ethylene oxide and glycidyltrimethylammonium chloride
Celquat HS 100 (Polyquaternium-4)
  Hydroxyethylcellulose modified cationically by reaction with diallyldimethylammonium chloride
Jaguar C 14 S
  Cationically modified guar gum
Carbopol 940 (carbomer)
  Crosslinked polyacrylic acid

TABLE 2

Examples of pump foams, with performance tests

| Base material<br>Amounts in g | Example 8 | Example 9<br>(Comparative Example) | Example 10<br>(Comparative Example) | Example 11<br>(Comparative Example) |
|---|---|---|---|---|
| Luvimer MAE 30 D (MAA/EA copolymer) | 1.67<br>(0.5% a.i.) | 3.33 | — | 1.67<br>(0.5% a.i.) |
| 2-Amino-2-methyl-1-propanol | 0.13 | 0.29 | — | 0.13 |
| Luviquat Hold (Polyquaternium-46) | 2.50<br>(0.5% a.i.) | — | 5.00<br>(1.00% a.i.) | 2.50<br>(0.5% a.i.) |
| Cremophor A 25 | 0.50 | 0.50 | 0.50 | 0.50 |
| Tego-Betain L7 | 1.00 | 1.00 | 1.00 | 1.00 |
| Cremophor RH 40 | 0.70 | 0.70 | 0.70 | 0.70 |
| Perfume oil | 0.20 | 0.20 | 0.20 | 0.20 |
| Preservative Euxyl K 100 | 0.10 | 0.10 | 0.10 | 0.10 |
| Propane/butane 25:75 | — | — | — | 10.00 |
| Water | ad 100.00 g | ad 100.00 g | ad 100.00 g | ad 100.00 g |
| Performance tests | | | | |
| Foam stability | very good | very good | very good | very good |
| Flexural strength | 142 cN | 103 cN | 63 cN | 142 cN |
| Curl retention | 50% | 39% | 35% | 50% |
| Stickiness | 1 | 2 | 1 | 1 |
| Half-side test on headform: | | | | |
| Ease of foam distribution on the hair | very good | very good | very good | moderate |
| Wet combability | good | poor | good | good |
| Setting effect | very good | moderate | good | very good |
| Dry combability | very good | very good | moderate | very good |
| Feel of the hair | very good | good | good | very good |

Description of the Test Methods

Foam stability:

The stability of the foam was assessed using an amount the size of a tennis ball. In the case of the pump foams (Examples 8 to 10) about eight strokes were required to obtain this amount (Pumpsystems from Airspray, model F2 Finger Pump Foamer).

The assessment was based on the following ratings scale:

very good: after application to the hand, the foam remains unchanged for more than 2 minutes, good: after application to the hand, the foam remains unchanged for more than 1 minute, poor: the foam immediately breaks down.

A) Flexural Strength, Curl Retention and Stickiness

Flexural strength

Pretreatment of the hair switches

Hair switches with a length of 20 cm and a weight of from 2.2 to 2.6 g were soaked in the abovementioned formulation, pressed off lightly on filter paper and dried overnight at 20° C. and 65% relative humidity.

The hair switches were placed symmetrically on two cylindrical rollers (diameter 6 mm, distance between the two rollers 9 cm). In the center of the two points of switch/roller contact a tensile/pressure testing machine was used to exert an increasing force on the switches. The maximum force exerted before the treated hair switches fold is stated in centiNewtons (cN). It is a measure of the setting effect of polymers on hair. Each polymer solution was tested on 10 different hair switches.

Stickiness

The test solutions (see Table) were applied to a glass plate using a doctor blade with a gap width of 120 $\mu$m. The wet film was stored overnight in a climatically controlled cabinet at 75% relative humidity and at 20° C. A plastic-carbon ribbon (Pelikan 2060, 50 mm wide) was placed on a glass plate that had been coated with the solutions. A rubber stamp of Shore A hardness 60+5 was used to exert a force of 250 N for 10 s. The test was carried out in the climatically controlled cabinet at 75% relative humidity. To the extent to which the solution surface is sticky, the printing ink of the carbon ribbon remains adhering on the polymer film (Assessment: ratings from 0=not sticky to 5=very sticky, >5: polymer film is torn away from the glass plate).

Curl retention

The curl retention was determined using hair switches weighing 2 g and measuring 15.5 cm in length, composed of medium-brown European human hair.

Method of determination

The hair switches were stored for 1 hour in an ethanol/water solution (1:1), rinsed with water and then washed twice with an aqueous solution of Texapon NSO (approximately 0.5% a.i.). The hair switches were then rinsed with water at about 40° C. until no further soaping was evident, combed and stored in water.

The wet switches were then immersed three times in the above-described solutions (see above); between each immersion they were stripped of excess solution using the fingers and were pressed between filter paper. The hair was then wound around a Teflon rod (12 mm in diameter) and fastened with filter paper and a rubber ring. The hair switches were then dried in a hot oven at 70° C. for 90 minutes. After cooling to room temperature, the tresses were removed from the rod and suspended on a Plexiglas frame produced specifically for this purpose, and the tress length (L0) was measured against the attached scale.

In order to determine a curl retention value, 10 tresses were used. The tresses were placed in a climatically controlled chamber at 20° C. and 75% relative atmospheric humidity. Their lengths (Lt) were measured after 5 hours.

The curl retention is calculated as follows:

$$\text{Curl Retention in \%} = \frac{L - Lt}{L - L0} * 100$$

L=Length of the hair (15.5 cm)
L0=Length of the tresses after drying
Lt=Length of the tresses after climatic treatment The curl retention stated is the mean of the 10 individual measurements after 5 h at 20° C. and 75% relative humidity.

B) Half-side Headform Test

Ease of distribution of the foam on the headforms

The ease of distribution of the foam on headforms with human hair was assessed by at least three persons. Their assessment was based on the following ratings scale:

very good: great ease of distribution; the foam is soft and breaks down as soon as it comes into contact with hair,
moderate: the foam is very firm, remains stable even after contact with the hair, and so is relatively difficult to incorporate.

The half-side tests were carried out in a climatically controlled area at 65% relative humidity and 20° C.

The headforms used were from HTS, with brown Central European human hair. The hair length was about 25 cm.

Before being treated with the hair foams, the headforms were washed with a solution of 14% sodium lauryl ether sulfate in water and rinsed thoroughly with water until there was no longer any foaming. The excess water was removed with a cloth and the wet hair was combed through thoroughly.

In each case, one half of the wet hair was treated with the formulation of Example 8. The other half in each case was treated with the formulations of Examples 9 and 10 (Comparative Examples).

The amount of foam applied corresponds in size to a tennis ball and was distributed uniformly.

Wet combability

The wet combability was assessed subjectively by at least three persons using separate combs. The ratings scale comprised the three assessments very good, good and poor. Very good and good denote that the hair is significantly easier to comb in the wet state than hair not treated with the respective hair foams.

Setting

After the hair had dried overnight, three persons assessed the setting of the hair by pressing the hair with the fingers. The ratings scale comprises three assessments: very good, good and moderate.

Dry combability

The hair is then combed out and the dry combability is determined (same rating scale and assessment as for wet combability).

Feel of the hair

The feel of the hair was likewise determined by at least three persons. The ratings scale ranges from very good (the hair feels smooth and compliant) through good (the hair feels similar to dry and untreated hair) to poor (the hair feels unpleasantly rough and dull).

TABLE 3

Examples of pump sprays

| Base material Amounts in g | Example 11 | Example 12 |
|---|---|---|
| Luvimer 36 D (MAA/t-BA/EA copolymer) | 4.17 (1.5% a.i.) | 6.94 (2.5% a.i.) |
| 2-Amino-2-methyl-1-propanol | 1.25 | 1.66 |
| Luviquat Hold (Polyquaternium-46) | 1.00 (0.2% a.i.) | 1.50 (0.3% a.i.) |
| Ethanol | 55.00 | 55.00 |
| Perfume oil | 0.10% | 0.10% |
| Water | ad 100.00 g | ad 100.00 g |

TABLE 4

Examples of hair-setting gels

| Base material Amounts in g | Example 11 | Example 12[3] |
|---|---|---|
| Luvimer MAE 30 D (MAA/EA copolymer) | 1.70 (0.5% a.i.) | 1.00 (0.3% a.i.) |
| 2-Amino-2-methyl-1-propanol | 0.55 | 0.25 |
| Luviquat Hold (Polyquaternium-46) | 2.50 (0.5% a.i.) | 1.50 (0.3% a.i.) |
| Carbopol 940 (Carbomer) | 0.50 | 0.30 |
| Euxyl K 100 | 0.10 | 0.10 |
| Water | ad 100.00 g | ad 100.00 g |

[3] the setting gel is sprayable in the form of a pump spray with the valve GMPS 38/200 + V04.1440 + V20.5 from Coster

We claim:

1. A hair treatment composition in the form of a pump spray or pump foam which is free from propellant gas, which composition comprises at least one cationic and at least one anionic polymer, said anionic polymer being a copolymer having methacrylic acid and ethyl acrylate units, wherein said cationic polymer is a copolymer having vinylpyrrolidone units.

2. A hair treatment composition in the form of a pump spray or pump foam which is free from propellant gas, which composition comprises at least one cationic and at least one anionic polymer, said anionic polymer being a copolymer having methacrylic acid and ethyl acrylate units and which composition has an pH from 5 to 8.

3. The pump spray or pump foam of claim 2, wherein said cationic polymer is a copolymer having vinylpyrrolidone units.

4. The pump spray or pump foam of claim 2, which comprises water, alcohol or a water/alcohol mixture as solvent.

* * * * *